US012590124B2

(12) United States Patent
Chung et al.

(10) Patent No.: US 12,590,124 B2
(45) Date of Patent: Mar. 31, 2026

(54) PEPTIDE WITH NEUTRALIZING ACTIVITY AGAINST SEVERE ACUTE RESPIRATORY SYNDROME CORONAVIRUS 2

(71) Applicant: CAREGEN CO, LTD., Anyang-si (KR)

(72) Inventors: Yong Ji Chung, Anyang-si (KR); Eun Mi Kim, Anyang-si (KR); Eung Ji Lee, Anyang-si (KR); Young Min Lee, Anyang-si (KR); Han A Kang, Anyang-si (KR); Min Kyeong Jeong, Anyang-si (KR)

(73) Assignee: CAREGEN CO, LTD., Anyang-si (KR)

( * ) Notice: Subject to any disclaimer, the term of this patent is extended or adjusted under 35 U.S.C. 154(b) by 602 days.

(21) Appl. No.: 18/016,046

(22) PCT Filed: Jul. 15, 2021

(86) PCT No.: PCT/KR2021/009080
§ 371 (c)(1),
(2) Date: Jan. 13, 2023

(87) PCT Pub. No.: WO2022/015069
PCT Pub. Date: Jan. 20, 2022

(65) Prior Publication Data
US 2024/0051993 A1      Feb. 15, 2024

(30) Foreign Application Priority Data
Jul. 16, 2020    (KR) ........................ 10-2020-0088076
Mar. 9, 2021    (KR) ........................ 10-2021-0030604

(51) Int. Cl.
*C07K 7/04*       (2006.01)
*A61P 31/14*      (2006.01)

(52) U.S. Cl.
CPC ................ *C07K 7/04* (2013.01); *A61P 31/14* (2018.01)

(58) Field of Classification Search
CPC .... C07K 7/04; C07K 7/06; C07K 7/08; A61P 31/14; G01N 33/56983; G01N 2333/165; G01N 2469/10; A61K 38/00
See application file for complete search history.

(56) References Cited

U.S. PATENT DOCUMENTS 7,728,110 B2      6/2010   Babcook et al.
9,017,968 B2*    4/2015   Wong .................... C07K 14/50
                                                                    435/70.1
(Continued)

FOREIGN PATENT DOCUMENTS

JP        H10-262668 A      10/1998
JP        2008-529504 A      8/2008
(Continued)

OTHER PUBLICATIONS

International Search Report and Written Opinion of the International Searching Authority for International Patent Application No. PCT/KR2021/009080 mailed Oct. 11, 2021 (10 pages).
(Continued)

*Primary Examiner* — Randall L Beane
(74) *Attorney, Agent, or Firm* — Merchant & Gould P.C.

(57) ABSTRACT
The present invention relates to a peptide that specifically recognizes a protein of severe acute respiratory syndrome coronavirus 2 (SARS-CoV-2) or a portion thereof; a composition for preventing or treating SARS-CoV-2 infection, comprising the peptide; and a composition for detecting SARS-CoV-2, comprising the peptide.

13 Claims, 3 Drawing Sheets
Specification includes a Sequence Listing.

(56) References Cited

U.S. PATENT DOCUMENTS

| | | | |
|---|---|---|---|
| 9,637,519 B2 * | 5/2017 | Chung | A61P 37/00 |
| 10,266,612 B2 | 4/2019 | Nurcombe et al. | |
| 10,344,061 B2 | 7/2019 | Chung et al. | |
| 2007/0160981 A1 | 7/2007 | Chen et al. | |
| 2008/0214469 A1 | 9/2008 | Lam et al. | |
| 2011/0262529 A1 | 10/2011 | Matsui et al. | |
| 2012/0171234 A1 | 7/2012 | Wong et al. | |
| 2013/0190241 A1 | 7/2013 | Wong et al. | |
| 2013/0190255 A1 | 7/2013 | Wong et al. | |
| 2014/0134673 A1 | 5/2014 | Wong | |
| 2016/0075739 A1 | 3/2016 | Chung et al. | |
| 2019/0092821 A1 * | 3/2019 | Chung | A61Q 19/00 |
| 2021/0355193 A1 | 11/2021 | Lee et al. | |
| 2023/0265169 A1 | 8/2023 | Lee et al. | |

FOREIGN PATENT DOCUMENTS

| | | | |
|---|---|---|---|
| JP | 2009-537143 A | 10/2009 | |
| JP | 5686370 B2 | 3/2015 | |
| JP | 2016-520587 A | 7/2016 | |
| JP | 2019-508490 A1 | 3/2019 | |
| KR | 10-1996-0015442 B1 | 11/1996 | |
| KR | 10-2008-0012449 A | 2/2008 | |
| KR | 10-2011-0005473 A | 1/2011 | |
| KR | 10-2014-0134083 A | 11/2014 | |
| KR | 10-2017-0105697 A | 9/2017 | |
| KR | 10-1895228 B1 | 10/2018 | |
| KR | 10-1916899 B1 | 11/2018 | |
| KR | 10-2019008 B1 | 9/2019 | |
| KR | 10-2081267 B1 | 2/2020 | |
| WO | 87/03885 A1 | 7/1987 | |
| WO | 2007-015918 A2 | 2/2007 | |

OTHER PUBLICATIONS

Extended European Search Report dated 06.06.2025 for corresponding EP Application No. 25161074.7 (7 pages).

Notice of Allowance issued on Dec. 27, 2023 for corresponding Korean Patent Application No. 10-2021-0109989 (10 pages including English Translation).

Notice of Allowance issued on Jan. 16, 2024 for corresponding Korean Patent Application 10-2021-0109990 (10 pages including English Translation).

Notice of Allowance issued on Jan. 16, 2024 for corresponding Korean patent applications 10-2021-0109991 (10 pages including English Translation).

First Office Action issued on Jan. 9, 2024 for the corresponding Japanese Patent Application No. 2023-502628 (15 pages including English Translation).

Partial European Search Report issued on Jan. 30, 2024 for the corresponding European Patent Application No. 21842944.7 (18 pages).

"Conidial yellow pigment biosynthesis polyketide synthase, partial [Pyricularia oryzae Y34]", Database Genbank [online], Mar. 19, 2015, Accession No. ELQ38032.1, https://www.ncbi.nlm.nih.gov/protein/ELQ38032.1/, (2 pages).

"Hypothetical protein H5410_048386 [Solanum commersonii]", Database GenBank [online], 2021.05.04, Accession No. KAG5587952.1, <https://www.ncbi.nlm.nih.gov/protein/kag5587952.1>, (2 pages).

"MAG: polyribonucleotide nucleotidyltransferase [Ignavibacteriales bacterium]", Database GenBank [online], 2020.12.21, Accession No. MBI3586173.1, https://www.ncbi.nlm.nih.gov/protein/mbi3586173.1, (2 pages).

Shuai Xia, et al., "Inhibition of SARS-CoV-2 (previously 2019-nCoV) infection by a highly potent pan-coronavirus fusion inhibitor targeting its spike protein that harbors a high capacity to mediate membrane fusion", Cell Research, Springer Nature, Mar. 2020, vol. 30, No. 4, 30, pp. 343-355.

Changhai Lei et al, "Neutralization of SARS-CoV-2 spike pseudotyped virus by recombinant ACE2-Ig", Nature Communications, Apr. 24, 2020, pp. 1-5.

Seth J. Zost, et al., "Rapid isolation and profiling of a diverse panel of human monoclonal antibodies targeting the SARS-CoV-2 spike protein", Nature Medicine, 2020, vol. 26, No. 9, pp. 1422-1427.

Zhang G., et al., "Investigation of ACE2 N-terminal fragments binding to SARS-CoV-2 Spike RBD", bioRxiv, Jun. 17, 2020, pp. 1-20.

* cited by examiner

SEQUENCE LISTING

```
<160> NUMBER OF SEQ ID NOS: 6

<210> SEQ ID NO 1
<211> LENGTH: 11
<212> TYPE: PRT
<213> ORGANISM: Artificial Sequence
<220> FEATURE:
<223> OTHER INFORMATION: Synthetic

<400> SEQUENCE: 1
```

```
Arg Ser Tyr Met Thr Thr His His Glu Gln Phe
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Synthetic

<400> SEQUENCE: 2

Lys Phe Asn Arg Arg His His
1               5

<210> SEQ ID NO 3
<211> LENGTH: 12
<212> TYPE: PRT
<213> ORGANISM: Artificial Sequence
<220> FEATURE:
<223> OTHER INFORMATION: Synthetic

<400> SEQUENCE: 3

Lys Tyr Leu Leu Val His Arg Pro Tyr Tyr Arg Arg
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Synthetic

<400> SEQUENCE: 4

Trp Val Pro Tyr Gln Ala Arg Val Pro Tyr Pro Arg
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Synthetic

<400> SEQUENCE: 5

Arg Leu Tyr Cys Lys Asn Gly Gly Phe Phe Leu Arg
1               5                   10

<210> SEQ ID NO 6
<211> LENGTH: 9
<212> TYPE: PRT
<213> ORGANISM: Artificial Sequence
<220> FEATURE:
<223> OTHER INFORMATION: Synthetic

<400> SEQUENCE: 6

Lys His Arg Gly Gly Gly Asn Arg Arg
1               5
```

PEPTIDE WITH NEUTRALIZING ACTIVITY AGAINST SEVERE ACUTE RESPIRATORY SYNDROME CORONAVIRUS 2

CROSS-REFERENCE TO RELATED APPLICATIONS

This application is a National Stage Application of PCT/KR2021/009080, filed 15 Jul. 2021, which claims benefit of Serial No. 10-2020-0088076, filed 16 Jul. 2020 and Serial No. 10-2021-0030604, filed 9 Mar. 2021 in Republic of Korea and which applications are incorporated herein by reference. To the extent appropriate, a claim of priority is made to each of the above disclosed applications.

SEQUENCE STATEMENT

This application contains a Sequence Listing, which has been submitted electronically in ASCII format and is hereby incorporated by reference in its entirety. Said ASCII copy, is named Sequence-Listing-09983-0265FPWO.TXT, was created on Sep. 15, 2023, and is 1737 bytes in size.

TECHNICAL FIELD

The present invention relates to a peptide having neutralizing activity against severe acute respiratory syndrome coronavirus 2 (SARS-Cov-2) and the use thereof.

BACKGROUND ART

Severe acute respiratory syndrome coronavirus 2 (SARS-Cov-2) is a single-stranded RNA virus that belongs to the subfamily Coronavirinae, and was first discovered in December 2019 in a patient with pneumonia of unknown cause in Wuhan, China. To avoid confusion with severe acute respiratory syndrome infection, the World Health Organization (WHO) also refers to it as "the coronavirus disease 2019 virus" or "the virus responsible for coronavirus disease 2019".

It is known that from December 2019 to early July 2020, 11.57 million confirmed cases occurred in 214 countries around the world, of which 537,138 died, and the fatality rate reaches 4.64. The clinical symptoms of SARS-CoV-2 are mainly respiratory symptoms accompanied by fever, and the main vulnerable subjects are the elderly in their 60s or older suffering from underlying diseases, immune diseases, and the like. Unlike previous viruses, it showed strong contagiousness and rapid worsening of symptoms, and in March 2020, about three months after the first outbreak was reported, the WHO declared a global epidemic, a pandemic.

There is no specific therapeutic agent yet, but it has been reported that research on antiviral agents was conducted, and antiviral drugs such as remdesivir, an RNA polymerase inhibitor, chloroquine, a malaria drug, and lopinavir/ritonavir, an antiretroviral human immunodeficiency I protease inhibitor, showed SARS-CoV-2 inhibitory effects at the cellular level. However, therapeutic agents that have been known to be effective so far have become problematic in actual clinical practice because their effects are insignificant or they can cause various side effects.

Accordingly, as a result of diligent efforts to develop a new therapeutic agent capable of inhibiting SARS-CoV-2, the present inventors have confirmed that the peptides of the present invention may be usefully used for preventing, ameliorating or treating coronavirus infection, and have completed the present invention.

DISCLOSURE

Technical Problem

It is an object of the present invention to provide a peptide that specifically recognizes a protein of severe acute respiratory syndrome coronavirus 2 (SARS-Cov-2) or a portion thereof.

It is another object of the present invention to provide a composition for preventing or treating SARS-CoV-2 infection.

It is still another object of the present invention to provide a method of preventing or treating SARS-CoV-2 infection.

It is still another object of the present invention to provide a composition for use in preventing or treating SARS-CoV-2 infection.

It is still another object of the present invention to provide a composition for detecting SARS-CoV-2.

It is still another object of the present invention to provide a method of detecting SARS-CoV-2.

It is still another object of the present invention to provide a composition for use in detecting SARS-CoV-2.

It is still another object of the present invention to provide a kit for diagnosing SARS-CoV-2 infection or disease.

Technical Solution

To these ends, an aspect of the present invention provides a peptide that specifically recognizes a protein of severe acute respiratory syndrome coronavirus 2 (SARS-Cov-2) or a portion thereof.

In addition, another aspect of the present invention provides a composition for preventing or treating SARS-CoV-2 infection, comprising the peptide.

In addition, another aspect of the present invention provides a method of preventing or treating SARS-CoV-2 infection, comprising administering the peptide or the composition comprising the peptide to a subject.

In addition, another aspect of the present invention provides the peptide or a composition comprising the peptide for use in preventing or treating SARS-CoV-2 infection.

In addition, another aspect of the present invention provides a composition for detecting SARS-CoV-2, comprising the peptide.

In addition, another aspect of the present invention provides a method of detecting SARS-CoV-2, comprising contacting the peptide or the composition comprising the peptide with a biological sample.

In addition, another aspect of the present invention provides the peptide or a composition comprising the peptide for use in detecting SARS-CoV-2.

Another aspect of the present invention provides a kit for diagnosing SARS-CoV-2 infection or disease.

Advantageous Effects

The peptide comprising an amino acid sequence selected from the group consisting of the amino acid sequences of SEQ ID NO: 1 to SEQ ID NO: 6 according to the present invention has the effect of inhibiting the membrane fusion of a virus and a host cell by binding to a spike protein on the surface of SARS-CoV-2 to neutralize SARS-CoV-2, and thus, it may be used for the purpose of preventing, treating or diagnosing SARS-CoV-2 infection.

However, the effects of the present invention are not limited to the effect mentioned above, and other effects that are not mentioned will be clearly understood by those skilled in the art from the following description.

BEST MODE

Figure 1:
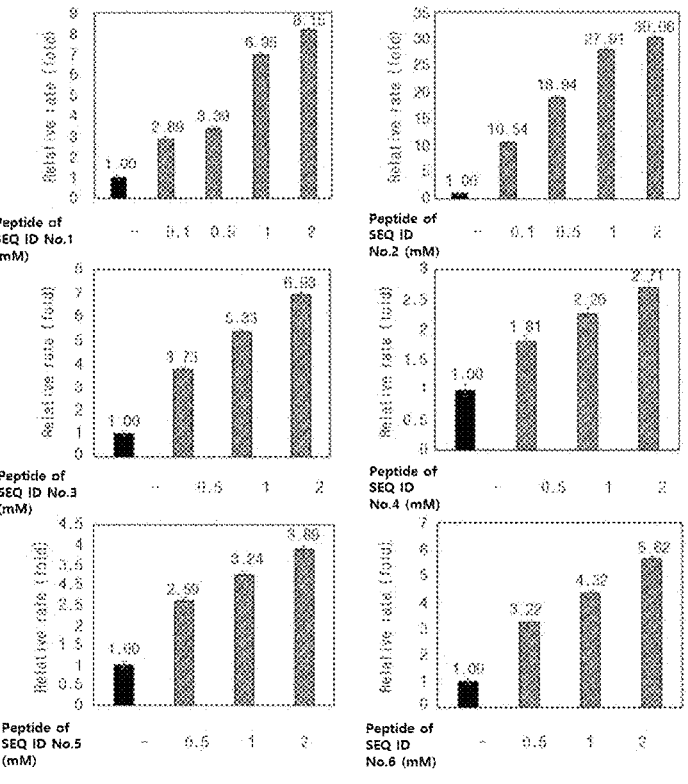
FIG. 1 is graphs showing the ELISA results of confirming the ability of the peptides of SEQ ID NOs: 1 to 6 according to the present invention to bind to the receptor binding domain (RBD) of the SARS-CoV-2 spike protein.

Hereinafter, the present invention will be described in detail.

An aspect of the present invention provides a peptide that specifically recognizes a protein of severe acute respiratory syndrome coronavirus 2 (SARS-CoV-2) or a portion thereof, comprising any one amino acid sequence selected from the group consisting of sequences of SEQ ID NO: 1 to SEQ ID NO: 6.

In the present specification, the term "peptide" refers to a linear or cyclic molecule formed by linking amino acid residues to each other by a peptide bond. The preparation of the peptide may be achieved by a conventional biological or chemical synthesis method known in the art, and as an example, it may be achieved by methods such as solid-phase synthesis techniques.

The "peptide" may be variants or fragments of amino acids having a different sequence by deletion, insertion or substitution of amino acid residues, or a combination thereof within a range that does not affect the function. Amino acid exchanges that do not entirely alter the activity of the peptide are known in the art. In some cases, it may be modified by phosphorylation, sulfation, acrylation, glycosylation, methylation, farnesylation, and the like. Accordingly, the present invention includes a peptide having an amino acid sequence substantially identical to a peptide comprising any one amino acid sequence selected from the group consisting of SEQ ID NOs: 1 to 6, and variants or active fragments thereof. The substantially identical protein refers to, but is not limited to, an amino acid sequence having 75% or more, preferably 80% or more, for example, 85% or more, 90% or more, 95% or more, 98% or more, or 99% or more sequence homology to any one amino acid sequence selected from the group consisting of SEQ ID NOs: 1 to 6, and if it has 75% or more amino acid sequence homology and has the same activity, it is included in the scope of the present invention. In addition, the peptides of the present invention may further comprise a targeting sequence, a tag, a labeled residue, and an amino acid sequence prepared for a specific purpose of increasing half-life or peptide stability.

In addition, in order to obtain better chemical stability, enhanced pharmacological properties (half-life, uptake, titer, efficacy, and the like), altered specificity (for example, a broad spectrum of biological activity), and reduced antigenicity, a protecting group may be attached to the N-terminus or C-terminus of the peptides of the present invention. For example, the protecting group may be an acetyl group, a fluorenylmethoxycarbonyl group, a formyl group, a palmitoyl group, a myristyl group, a stearyl group, or polyethylene glycol (PEG), but any component capable of enhancing the modification of the peptide, in particular, the stability of the peptide may be included without limitation. The "stability" is used as a meaning including not only in vivo stability that protects the peptides of the present invention from attack by in vivo protein cleaving enzymes, but also storage stability (for example, storage stability at room temperature).

In an embodiment, the peptides of the present invention are selected from the group consisting of:

RSYMTTHHEQF (SEQ ID NO: 1);

KFNRRHH (SEQ ID NO: 2);

KYLLVHRPYYRR (SEQ ID NO: 3);

WVPYQARVPYPR (SEQ ID NO: 4);

RLYCKNGGFFLR (SEQ ID NO: 5); and

KHRGGGNRR (SEQ ID NO: 6).

The peptides of the present invention may specifically bind to the spike protein (S protein) of SARS-CoV-2. More specifically, the peptides of the present invention may specifically bind to the RBD (receptor binding domain) present in the spike protein of SARS-CoV-2.

In the present specification, the term "specifically binding" means binding to the protein of interest, i.e., the RBD that is a spike protein of SARS-CoV-2 or a portion thereof, but not substantially recognizing and binding to other molecules in the sample.

The peptides of the present invention may specifically bind to a spike protein on the surface of SARS-CoV-2 to inhibit the binding of the spike protein to the cell membrane receptor of a host cell.

The cell membrane receptor of the host cell is angiotensin-converting enzyme 2 (ACE2), and the angiotensin converting enzyme 2 is a transmembrane protein found in eukaryotes and bacteria and is a receptor used by coronaviruses including SARS-CoV-2 to invade cells.

In an embodiment, it was confirmed that the peptides of the present invention may specifically bind to the spike protein RBD on the surface of SARS-CoV-2 to neutralize SARS-CoV-2, and may inhibit the binding of SARS-CoV-2 to the cell membrane of the host cell.

In the present specification, the term "neutralization" refers to the ability to inhibit the replication of SARS-CoV-2 in vivo and/or in vitro, regardless of the mechanism by which neutralization is achieved. In an embodiment, the peptides of the present invention neutralize SARS-CoV-2 by inhibiting SARS-CoV-2 from attaching to target cells to fuse the viral membrane with the cell membrane.

Another aspect of the present invention provides a pharmaceutical composition for preventing or treating severe acute respiratory syndrome coronavirus 2 (SARS-CoV-2) infection, comprising the peptide.

In addition, the present invention provides a method of preventing or treating SARS-CoV-2 infection, comprising administering the peptide or the composition comprising the peptide to a subject.

In addition, the present invention provides the peptide or a composition comprising the peptide for use in preventing or treating SARS-CoV-2 infection. The composition may prevent or treat SARS-CoV-2 infection by binding to a spike protein on the surface of severe acute respiratory syndrome coronavirus 2 to inhibit the binding of the spike protein to a cell membrane receptor of a host cell.

The pharmaceutical composition for preventing or treating SARS-CoV-2 infection according to the present invention may be formulated and used in the form of oral formulations such as powders, granules, tablets, capsules, suspensions, emulsions, syrups and aerosols, external preparations, suppositories and sterile injectable solutions according to conventional methods, respectively, and may further comprise a pharmaceutically acceptable carrier, excipient or diluent in addition to the peptide for formulation.

The pharmaceutically acceptable carriers may include lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methylcellulose, methylhydroxybenzoate, propylhydroxybenzoate, talc, magnesium stearate, mineral oil, and the like, which are commonly used in the formulations.

The pharmaceutical composition may further comprise a lubricant, a wetting agent, a sweetener, a flavoring agent, an emulsifier, a suspending agent, a preservative, and the like, in addition to the ingredients as described above.

The pharmaceutical composition may be administered orally or parenterally (for example, applied intramuscularly, intravenously, intraperitoneally, subcutaneously, intradermally, or locally) depending on the desired method, and the dosage varies depending on the condition and body weight of the patient, the severity of the disease, the form of the drug, the route and time of administration, but can be appropriately selected by those skilled in the art.

The pharmaceutical composition of the present invention is administered in a pharmaceutically effective amount. In the present invention, the term "pharmaceutically effective amount" refers to an amount sufficient to treat a disease at a reasonable benefit/risk ratio applicable to medical treatment, and the level of the effective dose may be determined depending on the factors including the type and severity of the patient's disease, the activity of the drug, the sensitivity to the drug, the time of administration, the route of administration and the rate of the excretion, the duration of treatment, and the drugs used simultaneously, and other factors well known in the medical field. The pharmaceutical composition may be administered as an individual therapeutic agent or administered in combination with other therapeutic agents, may be administered concurrently, separately, or sequentially with conventional therapeutic agents, and may be administered single or multiple times. Considering all of the above factors, it is important to administer an amount that can achieve the maximum effect in a minimal amount without side effects, which can be easily determined by those skilled in the art.

The effective amount of the pharmaceutical composition may vary depending on the age, sex, condition and body weight of the patient, the degree of absorption of the active ingredient into the body, the rate of the inactivation, the rate of the excretion, the type of disease, and concomitant drugs, and may be increased or decreased depending on the route of administration, the severity of obesity, sex, body weight, age, and the like, and, for example, the pharmaceutical composition may be administered in an amount of about 0.0001 µg to 500 mg, preferably 0.01 µg to 100 mg per 1 kg of patient's body weight per day.

The pharmaceutical composition of the present invention may further comprise at least one other therapeutic agent. For example, it may further comprise interferons, anti-S protein monoclonal antibodies, anti-S protein polyclonal antibodies, nucleoside analogs, DNA polymerase inhibitors, siRNA preparations or therapeutic vaccines as antiviral drugs together with the peptide. These may be used in combination with the peptides of the present invention. In the present specification, "in combination with" refers to following a regimen administered either simultaneously as separate formulations or as one single combined formulation, or sequentially in any order as separate formulations.

The "subject" may be a subject in need of administration of the peptide of the present application or a composition comprising the peptide, and the subject in need of the administration may include a subject diagnosed with SARS-CoV-2 infection, a subject with developed symptoms of SARS-CoV-2 infection, as well as a subject wishing to be administered to prevent the development of the disease or symptom or to improve health.

The "administration" refers to providing a predetermined substance to a patient by any appropriate method, and the peptides of the present invention may be administered orally or parenterally through all general routes as long as it can reach a desired tissue. In addition, the peptide or the composition comprising the peptide may be administered by any device capable of transporting an active substance to a target cell.

In another aspect, the present invention provides a pharmaceutical composition for detecting severe acute respiratory syndrome coronavirus 2 (SARS-CoV-2), comprising the peptide.

In addition, the present invention provides a method of detecting SARS-CoV-2, comprising contacting the peptide or the composition comprising the peptide with a biological sample.

In addition, the present invention provides the peptide or a composition comprising the peptide for use in detecting SARS-CoV-2.

The composition for detecting SARS-CoV-2 according to the present invention may be used to detect the presence or absence of SARS-CoV-2 in a biological sample by confirming the reaction after contacting the peptide with the biological sample.

The peptides of the present invention may be labeled to be detectable. Examples of labels that can be used in the present invention include enzymes, radioisotopes, colloidal metals, fluorescent compounds, chemiluminescent compounds, and bioluminescent compounds. Commonly used labels include fluorescent substances (for example, fluorescein, rhodamine, Texas red, and the like), enzymes (for example, horseradish peroxidase, R-galactosidase, alkaline phosphatase), radioisotopes (for example, 32P or 125I), biotin, digoxigenin, colloidal metals, chemiluminescent or bioluminescent compounds (for example, dioxetane, luminol or acridinium). Labeling methods such as covalent bonding of enzymes or biotinyl groups, iodination, phosphorylation and biotinylation are well known in the art.

Detection of the presence of SARS-CoV-2 may be performed by any one selected from the group consisting of enzyme-linked immunosorbent assay (ELISA), Western blotting, immunofluorescence, immunohistochemistry staining, flow cytometry, immunocytochemical assay, radioimmunoassay (RIA), immunoprecipitation assay, immunodiffusion assay, complement fixation assay, and protein chip.

The enzyme-linked immunosorbent assay (ELISA) includes various ELISA methods such as direct ELISA using a labeled antibody recognizing the peptide attached to a solid support, and indirect ELISA using a labeled secondary antibody recognizing the capture antibody in a complex of antibodies recognizing the peptide attached to a solid support.

The biological sample may be any one selected from the group consisting of, but is not limited to, sputum, spit, blood, sweat, respiratory tissue and saliva of a subject, and the sample may be prepared by a conventional method known in the art.

The present invention also provides a kit for diagnosing SARS-CoV-2 infection or disease, comprising the peptide.

In the present specification, the term "SARS-CoV-2 infection or disease" refers to a pathological condition resulting from infection of a cell or subject by SARS-CoV-2, and, for example, the disease may be a respiratory disease caused by SARS-CoV-2.

In the diagnostic kit of the present invention, the kit may comprise a solid carrier. The peptides of the present invention may be attached to the solid carrier, and such a solid carrier may be porous or non-porous, planar or non-planar.

Best Mode

Hereinafter, the present invention will be described in detail by way of examples and experimental examples.

However, the following examples and experimental examples are only for illustrating the present invention, and the content of the present invention is not limited to the following examples and experimental examples.

Example 1

Selection of Peptides of the Present Invention

In order to develop a peptide that inhibits the binding of a spike protein (S protein) of SARS-CoV-2 to angiotensin-converting enzyme 2 (ACE2), six peptides were selected from the peptide libraries through screening. The sequences of the selected peptides and the molecular weights of the peptides measured using a molecular weight meter are shown in Table 1 be low.

TABLE 1

| No. | Sequence | Molecular weight (Da) | SEQ ID NO: |
|-----|----------|----------------------|------------|
| 1 | RSYMTTHHEQF | 1437 | 1 |
| 2 | KFNRRHH | 994.1 | 2 |
| 3 | KYLLVHRPYYRR | 1664 | 3 |
| 4 | WVPYQARVPYPR | 1532 | 4 |
| 5 | RLYCKNGGFFLR | 1474 | 5 |
| 6 | KHRGGGNRR | 1037 | 6 |

Example 2

Confirmation of the Ability of the Peptides of the Present Invention to Bind to the SARS-CoV-2 Spike Protein RBD In order to confirm whether the peptides of the present invention may block the invasion of SARS-CoV-2 into host cells, first, it was confirmed whether the peptides of the present invention may recognize and bind to RBD in the spike protein of SARS-CoV-2.

Specifically, the six peptides selected in Experimental Example 1 were mixed with 2 mM sodium bicarbonate in equal volume and dispensed in 100 μL each in a 96-well plate, and then cultured overnight at 4° C. to coat the surface of the well with the peptides. They were washed three times with 0.1% PBS-T (0.1% Tween-20 in PBS), and then 100 μL of 3% BSA was dispensed, and then blocked at room temperature for 1 hour and washed three times with 0.1% PBS-T. Thereafter, they were treated with 100 ng of recombinant SARS-CoV-2 spike RBD-His (Sino Biological, Cat. No.: 40592-V08B, China) per well and reacted at room temperature for 2 hours. They were washed three times with 0.1% PBS-T, and then treated with anti-His antibody-HRP (Abcam, Cat. No.: ab1187, US) diluted 1:1000 in PBS and reacted at room temperature for 1 hour, and then washed three times with 0.1% PBS-T. 100 μL of TMB solution (ThermoFisher, Cat. No.: N301, US) was dispensed and reacted for about 5 minutes, and then the reaction was terminated by treatment with 50 μL of 1 M sulfuric acid. O.D. values were measured at a wavelength of 450 nm using a spectrometer.

As a result, as shown in FIG. 1, when the binding pattern of each of the peptides of SEQ ID NOs: 1 to 6 to RBD was observed by ELISA, it was confirmed that the binding fold of the peptides to RBD increased in a concentration-dependent manner.

From the above, it can be seen that the peptides of the present invention have the ability to recognize and bind to the RBD of the SARS-CoV-2 spike protein.

Example 3

Confirmation of the Ability of the Peptides of the Present Invention to Inhibit ACE2-RBD Binding In order to confirm whether the peptides of the present invention may block the invasion of SARS-CoV-2 into host cells, it was confirmed whether the peptides of the present invention inhibit the binding of ACE2, which is a membrane protein of host cells, to the SARS-CoV-2 RBD.

Specifically, 2 mM sodium bicarbonate and ACE2-FC protein (Sino Biological, Cat. No.: 10108-H02H, China) were mixed in equal volume and dispensed in 100 ng/100 μL/well in a 96-well plate, an then cultured overnight at 4° C. to coat the surface of the well with ACE2 protein. They were washed three times with 0.1% PBS-T (0.1% Tween-20 in PBS), and then 100 μL of 3% BSA was dispensed, and then blocked at room temperature for 1 hour. 100 ng of recombinant SARS-CoV-2 spike RBD His (Sino Biological, Cat. No.: 40592-V08B, China) was mixed with a peptide solution at each concentration in PBS and reacted at room temperature for 1 hour. The wells were washed 3 times with 0.1% PBS-T, and then the wells were treated with the protein-peptide mixture. They were reacted at room temperature for 2 hours, and then washed three times with 0.1% PBS-T. They were treated with anti-His antibody-HRP (Abcam, Cat. No.: ab1187, US) diluted 1:1000 in PBS and reacted at room temperature for 1 hour, and then washed three times with 0.1% PBS-T. 100 μL of TMB solution (ThermoFisher, Cat. No.: N301, US) was dispensed and reacted for about 5 minutes, and then the reaction was terminated by treatment with 50 μL of 1 M sulfuric acid. O.D. values were measured at a wavelength of 450 nm using a spectrometer.

Figure 2:
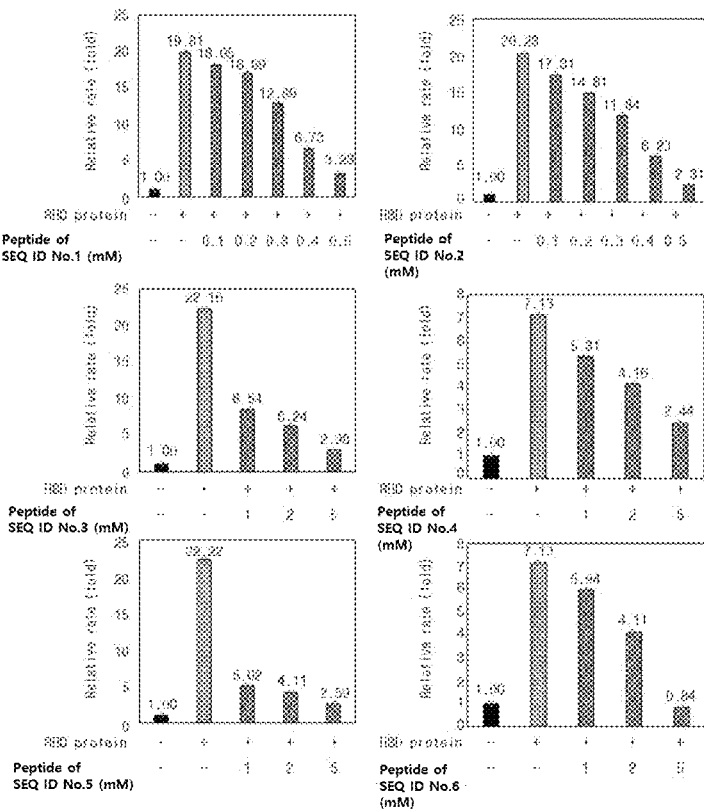
FIG. 2 is graphs showing the ELISA results of confirming the activity of the peptides of SEQ ID NOs: 1 to 6 according to the present invention to inhibit the binding of the SARS-CoV-2 spike protein RBD to the angiotensin-converting enzyme 2 (ACE2) protein of the host cell.

As a result, as shown in FIG. 2, it was confirmed that each of the peptides of SEQ ID NOs: 1 to 6 inhibited the binding of RBD to the ACE2 protein in a concentration-dependent manner.

From the above, it can be seen that the peptides of the present invention bind to the RBD of the SARS-CoV-2 spike protein to inhibit the binding of the spike protein to the ACE2 protein.

Example 4

Confirmation of the Ability of the Peptides of the Present Invention to Inhibit ACE2-RBD Binding in Human Lung Cancer Cells In order to confirm whether the peptides of the invention have the ability to prevent, ameliorate and treat coronavirus infection in mammalian cells, it was confirmed whether the ability of the SARS-CoV-2 spike protein RBD to bind to ACE2 of host cells is reduced after a human lung cancer cell line were treated with the peptides.

Specifically, A549 cells (Korean Cell Line Bank, Cat. No.: 10185, Korea), which are a human lung cancer cell line (adenocarcinomic human alveolar basal epithelial cells), were inoculated in a 6-well plate at a density of $5 \times 10^5$ cells/well and cultured for 24 hours. 500 ng of recombinant SARS-CoV-2 spike RBD His (Sino Biological, Cat. No.: 40592-V08B, China) was mixed with a peptide solution at each concentration in 1 mL of DMEM medium and reacted at room temperature for 1 hour. A549 cells cultured for one day were washed with DMEM medium, and then 900 μL of recombinant SARS-CoV-2 spike RBD/peptide mixture was added to the cells. After culturing for 2 hours in a $CO_2$ incubator at 37° C., the cells were washed twice with PBS and treated with 200 μL of lysis buffer to lyse the cells. Samples were prepared by treatment with 5× sample buffer, and then SDS-PAGE was performed using a 10% SDS-PAGE gel. Proteins separated through SDS-PAGE were transferred to a PVDF membrane, and then blocked using 5% skim milk at room temperature for 1 hour. Next, anti-His antibody-HRP (Abcam, Cat. No.: ab1187, US) was diluted 1:1000 in 5% skim milk, reacted with the membrane for 2 hours, and washed three times with 0.1% PBS-T (0.1% Tween-20 in PBS) for 10 minutes. It was detected as a film using an ECL solution (GE Healthcare, Cat. No.: RPN2232, US).

Figure 3:
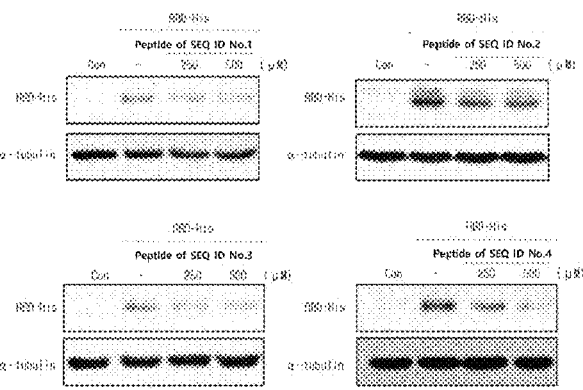
FIG. 3 shows the Western blot results of confirming whether the peptides of SEQ ID NOs: 1 to 4 according to the present invention have the ability to inhibit the binding of RBD to ACE2 expressed on the cell surface of human lung cancer cell line A549.

As a result, as shown in FIG. 3, it was confirmed that each of the peptides of SEQ ID NOs: 1 to 4 according to the present invention inhibited the binding of the SARS-CoV-2 spike RBD to ACE2 of host cells in a concentration-dependent manner.

From the above, it can be seen that the peptides of the present invention may prevent or treat virus infection in host cells by binding to the spike protein of SARS-CoV-2 to inhibit the binding of the spike protein to ACE2 of host cells.

Example 5

Confirmation of the Effect of the Peptides of the Present Invention to Inhibit SARS-CoV-2 Cell Infection In order to directly confirm whether the peptides of the present invention have the effect of inhibiting cell infection by SARS-CoV-2, a focus reduction neutralizing test (FRNT) was performed.

Specifically, Vero E6 cells (ATCC, USA) were inoculated in a 96-well plate at a density of $2 \times 10^4$ cells/well, and then cultured until 90-100% confluency. 500 focus-forming units (FFU)/well of SARS-CoV-2 and peptide samples at each concentration were mixed in a 1:1 ratio, and reacted at 37° C. for 1 hour. A monolayer of Vero E6 cells was treated with the mixture of peptide and virus, and culture at 37° C. for 1 hour. The supernatant was removed, and then treated with DMEM medium containing 1.6% carboxymethylcellulose (CMC) and cultured at 37° C. for 24 hours. The supernatant was removed, and then the cells were fixed with 4% paraformaldehyde and washed with PBS. Cell permeabilization was performed for 30 minutes by treatment with PBS containing 0.2% Triton X-100 and 1% BSA, and then washed with PBS. The cells were treated for 1 hour with the primary antibody against SARS-CoV-2 nucleocapsid (Sino Biological, China) diluted 1:1000 in PBS containing 1% BSA, and washed with PBST (PBS containing 1% Tween-20). The cells were treated for 1 hour with the secondary antibody (Sino Biological, China) diluted 1:2000 in PBS containing 1% BSA, and washed with PBST. They were treated with KPL TrueBlue™ Peroxidase Substrate (SeraCare Life Sciences, USA), and then washed with distilled water, and the number of SARS-CoV-2 foci was analyzed by Elispot reader (Cellular Technology Limited, USA). The inhibition rate against viral infection was calculated using the following equation:

$$\text{Inhibition rate against virus infection (\%)} = \text{(number of foci in the control group−number of foci in the treated group)/number of foci in the control group} \times 100 \quad \text{Equation 1}$$

As a result, as shown in Table 2, it was confirmed that when treated with the peptides of SEQ ID NOs: 1 to 4 according to the present invention, the inhibition rate against viral infection increased in a concentration-dependent manner for all four peptides.

From the above, it can be seen that the peptides of the present invention may prevent, ameliorate and treat SARS-CoV-2 infection by inhibiting cell infection by SARS-CoV-2.

TABLE 2

| SEQ ID NO: | Concentration (mM) | Inhibition rate (%) |
|---|---|---|
| 1 | 2.5 | 21 |
|   | 10 | 100 |
| 2 | 2.5 | 51 |
|   | 10 | 96 |
| 3 | 2.5 | 98 |
|   | 10 | 98 |
| 4 | 2.5 | 55 |
|   | 10 | 98 |

The invention claimed is:

1. A peptide comprising SEQ ID NO: 1 for recognizing a protein of severe acute respiratory syndrome coronavirus 2 (SARS-CoV-2).

2. A pharmaceutical composition for treating severe acute respiratory syndrome coronavirus 2 (SARS-CoV-2) infection, comprising the peptide of claim 1.

3. The pharmaceutical composition according to claim 2, wherein the composition binds to a spike protein on the surface of severe acute respiratory syndrome coronavirus 2 to inhibit the binding of the spike protein to a cell membrane receptor of a host cell.

4. The pharmaceutical composition according to claim 2, wherein the pharmaceutical composition further comprises a pharmaceutically acceptable carrier, excipient or diluent.

5. The pharmaceutical composition according to claim 2, wherein the pharmaceutical composition is suitable for oral administration, administration by injection, or external administration.

6. A composition for detecting severe acute respiratory syndrome coronavirus 2 (SARS-CoV-2), comprising the peptide of claim 1.

7. A method for treating severe acute respiratory syndrome coronavirus 2 (SARS-CoV-2) infection, the method comprising administering a therapeutically effective amount of the peptide of claim 1 to a subject in need thereof.

8. A method for detecting severe acute respiratory syndrome coronavirus 2 (SARS-CoV-2), the method comprising contacting a biological sample suspected of containing SARS-CoV-2 with the peptide of claim 1.

9. The method according to claim 8, wherein the peptide is labeled.

10. The method according to claim 9, wherein the label is selected from the group consisting of enzymes, radioisotopes, colloidal metals, fluorescent compounds, chemiluminescent compounds, bioluminescent compounds, and combinations thereof.

11. The method according to claim 10, wherein the fluorescent compound is selected from the group consisting of fluorescein, rhodamine, and Texas red.

12. The method according to claim 10, wherein the enzyme is selected from the group consisting of horseradish peroxidase, $\beta$-galactosidase, and alkaline phosphatase.

13. A method for inhibiting the binding of a spike protein of severe acute respiratory syndrome coronavirus 2 (SARS-CoV-2) to an angiotensin-converting enzyme 2 (ACE2) receptor on a host cell in a subject, the method comprising administering an effective amount of the peptide of claim 1 to the subject.

\* \* \* \* \*